United States Patent
Parker et al.

(10) Patent No.: US 11,049,592 B2
(45) Date of Patent: Jun. 29, 2021

(54) MONITORING ADHERENCE TO HEALTHCARE GUIDELINES

(71) Applicant: Ki Health Innovation Limited, London (GB)

(72) Inventors: Thomas Parker, London (GB); Kirstie Tew, London (GB)

(73) Assignee: KI PERFORMANCE LIFESTYLE LIMITED

( * ) Notice: Subject to any disclaimer, the term of this patent is extended or adjusted under 35 U.S.C. 154(b) by 322 days.

(21) Appl. No.: 15/316,348

(22) PCT Filed: Jun. 3, 2015

(86) PCT No.: PCT/GB2015/051622
§ 371 (c)(1),
(2) Date: Dec. 5, 2016

(87) PCT Pub. No.: WO2015/185927
PCT Pub. Date: Dec. 10, 2015

(65) Prior Publication Data
US 2017/0161462 A1    Jun. 8, 2017

(30) Foreign Application Priority Data

Jun. 4, 2014 (GB) .................................... 1409929

(51) Int. Cl.
*G16H 10/60* (2018.01)
*G16H 20/30* (2018.01)
(Continued)

(52) U.S. Cl.
CPC ............ *G16H 10/60* (2018.01); *A61B 5/1118* (2013.01); *A61B 5/4866* (2013.01); *G16H 20/30* (2018.01); *G16H 50/20* (2018.01); *G16H 50/30* (2018.01)

(58) Field of Classification Search
None
See application file for complete search history.

(56) References Cited

U.S. PATENT DOCUMENTS

2007/0027367 A1    2/2007  Oliver et al.
2007/0173705 A1*   7/2007  Teller ................. A61B 5/02055
                                                         600/300
(Continued)

FOREIGN PATENT DOCUMENTS

| WO | WO2006/006092 A1 | 1/2006 | |
|----|---|---|---|
| WO | 2011/032016 A1 | 3/2011 | |
| WO | WO-2011032016 A1 * | 3/2011 | ............... A61B 5/01 |

OTHER PUBLICATIONS

"Metabolic Equivalent", Wikipedia, the free encyclopedia, https://en.wikipedia.org/wiki/Metabolic_equivalent, screen capture Dec. 5, 2016.
(Continued)

*Primary Examiner* — Aryan E Weisenfeld
*Assistant Examiner* — Karen A Hranek
(74) *Attorney, Agent, or Firm* — Fish IP Law, LLP

(57) ABSTRACT

Systems and methods are disclosed for monitoring adherence to healthcare guidelines defining a recommended level of physical activity. Metabolic Equivalent (MET) data for a user over a plurality of days is analysed to determine whether sufficient MET data is available, by determining whether the obtained MET data includes at least a minimum amount of MET data within a defined time period. In response to a determination that sufficient MET data is available, the MET data is compared to guideline MET values relating to the recommended level of physical activity, to determine whether the user has achieved the recommended level of physical activity. An adherence result is outputted in accordance with the result of the comparison, indicating whether the user has achieved the recommended level of physical activity. The adherence result can be outputted in the form of a message displayed on a display unit. In some embodiments when MET data is captured over a plurality of days, it can be checked whether data has been (Continued)

captured for at least a minimum required number of days within a time period, for example one week.

15 Claims, 10 Drawing Sheets

(51) Int. Cl.
    *A61B 5/11*     (2006.01)
    *G16H 50/30*     (2018.01)
    *G16H 50/20*     (2018.01)
    *A61B 5/00*     (2006.01)

(56) References Cited

U.S. PATENT DOCUMENTS

| | | | |
|---|---|---|---|
| 2010/0137106 A1 | 6/2010 | Oshima et al. | |
| 2011/0087137 A1* | 4/2011 | Hanoun | G16H 40/67 600/587 |
| 2012/0059664 A1* | 3/2012 | Georgiev | A61B 5/02 705/2 |
| 2013/0158368 A1* | 6/2013 | Pacione | A61B 5/0022 600/301 |
| 2013/0190008 A1* | 7/2013 | Vathsangam | H04M 1/00 455/456.1 |
| 2013/0191034 A1 | 7/2013 | Weast et al. | |
| 2013/0246088 A1* | 9/2013 | Huster | G06Q 10/0635 705/2 |
| 2013/0282157 A1* | 10/2013 | Shin | A63B 24/0062 700/91 |
| 2014/0188400 A1* | 7/2014 | Dunn | A61B 5/7275 702/19 |

OTHER PUBLICATIONS

European Examination Report, European Patent Application No. 15728103.1 dated Aug. 4, 2019, 7 pages.

* cited by examiner

MONITORING ADHERENCE TO HEALTHCARE GUIDELINES

TECHNICAL FIELD

The present invention relates to monitoring adherence to healthcare guidelines. More particularly, the present invention relates to a system and method for monitoring a user's adherence to healthcare guidelines which define a recommended level of physical activity.

BACKGROUND OF THE INVENTION

In many areas of healthcare, patients are often given guidelines to follow in an attempt to improve patient outcomes. The healthcare guidelines are intended to encourage a positive behavioural change, for example to treat or manage an existing condition or prevent an unwanted condition arising. Many healthcare guidelines, particularly those relating to the prevention and rehabilitation of conditions such as cardiovascular disease or obesity, define a recommended level of physical activity. One example of healthcare guidelines which define a recommended level of physical activity is cardiac rehabilitation (CR) guidelines.

The number of patients eligible for CR programmes increases year-on-year. A total of 238,781 eligible patients (Myocardial Infarction [MI], Coronary Artery Bypass Graft [CABG] and Percutaneous Coronary Intervention [PCI]) across England were recorded in 2009/2010. Furthermore, it is recommended that CR is available to patients with stable angina (The Scottish Intercollegiate Guidelines Network [SIGN], 2002) and patients diagnosed with unstable angina and non-ST-segment-elevation myocardial infarction (NSTEMI; The National Institute for Health and Care Excellence [NICE] CG94, 2010). This further expands the scope of CR to the approximately 2 million people in England who have or have had angina (NICE CG126, 2011).

NICE defines CR as "a structured set of services that enables people with coronary heart disease (CHD) to have the best possible help (physical, psychological, social) to preserve or resume their optimal functioning in society". The benefits of completing CR programmes are well established, and include positive behavioural changes such as smoking cessation, physical activity status, physical fitness, anxiety and depression, in addition to positive clinical outcomes such as reduced cholesterol and systolic blood pressure.

At present, adherence to a CR regime is monitored through attendance at structured, supervised exercise and education sessions attended once or twice a week for the duration of the CR programme. CR guidelines prescribe an ideal intensity for physical activity using the heart rate, Borg Rating of Perceived Exertion (RPE) or CR10 equivalent of 40-60% individual $VO_2$ max, progressing to 70% individual $VO_2$ max, as appropriate. Throughout these supervised exercise sessions, patients are closely monitored to ensure they remain within their individually prescribed ideal heart rate and/or Borg RPE or CR10 range. It is advised that any physical activity completed at home is also completed within the same Borg RPE or CR10 range. A drawback of this approach is that both Borg RPE and CR10 are subjective ratings; the individual rates how hard they feel they are working against a number from 6 to 20 on the RPE scale and 0 to 10 on the CR10 scale. Heart rate is an objective measure, but is influenced by a number of factors not related to the activity being undertaken, such as emotional state, diet and medication.

The invention is made in this context.

SUMMARY OF THE INVENTION

According to the present invention, there is provided a system for monitoring adherence to healthcare guidelines defining a recommended level of physical activity, the system comprising: a data collection unit configured to obtain Metabolic Equivalent (MET) data for a user over a plurality of days; a data processing unit configured to: determine whether sufficient MET data is available by determining whether the obtained MET data includes at least a minimum amount of MET data within a defined time period, obtain guideline MET values relating to the recommended level of physical activity, and compare the received MET data to the guideline MET values in response to a determination that sufficient MET data is available to determine whether the user has achieved the recommended level of physical activity; and an output unit configured to output an adherence result indicating whether the user has achieved the recommended level of physical activity, in accordance with the result of the comparison. For example, the defined time period may be a 24-hour time period.

The data processing unit can be further configured to derive a value of an activity measure from the MET data, and compare the value of the activity measure to one or more thresholds associated with a risk of one or more health conditions to determine whether the user is at risk of any of the one or more health conditions, and the output unit can be configured to output a health risk result identifying any of the one or more health conditions to which the user may be at risk, according to the result of the comparison. The activity measure can be any suitable metric relating to the user's activity as determined from the MET data. For example, the activity measure can be: a measure of sedentary or non-sedentary time; a measure of calorie burn such as the Physical Activity Level (PAL); a measure of the total number of minutes of physical activity above a MET threshold in bouts of certain duration; and a measure of physical activity energy expenditure.

The data processing unit can be further configured to obtain user state information relating to a state of the user when the MET data was captured, and to determine a length of an inactive time period in which the user state information indicates an inactive state during said one of the plurality of days, wherein in response to the inactive time period being longer than a threshold time, the data processing unit is configured to determine that sufficient MET data is available if MET data is available for at least a predefined fraction of a remaining part of said day, wherein the remaining part excludes the inactive time period, and wherein in response to the inactive time period being shorter than the threshold time, the data processing unit is configured to determine that sufficient MET data is available if at least a predefined amount of MET data is available during the remaining part of said day.

The MET data can include data captured over a plurality of days, and the data processing unit can be further configured to determine whether MET data is available for at least a minimum number of days within a time period, and to only perform the comparison to the guideline MET values for MET data captured during the time period in response to a determination that MET data is available for at least the minimum number of days.

The data processing unit can be configured to determine whether the user has exceeded a limit set by the healthcare guidelines, and in response to a determination that the user has exceeded the limit, the output unit can be configured to output a message indicating a time at which the limit was exceeded.

The output unit can be configured to control a display unit to display the adherence result in the form of a message indicating whether the user has achieved the recommended level of physical activity.

The data collection unit can be configured to obtain MET data captured substantially continuously over at least an 8-hour period.

In some embodiments, the data collection unit can comprise a network interface configured to receive the MET data over a network connection. In other embodiments, the data collection unit can comprise a MET sensor arranged to directly capture the MET data.

According to the present invention, there is also provided a method of monitoring adherence to healthcare guidelines defining a recommended level of physical activity, the method comprising: obtaining guideline MET values relating to the recommended level of physical activity; obtaining MET data for a user captured over a plurality of days; determining whether sufficient MET data is available by determining whether the obtained MET data includes at least a minimum amount of MET data within a defined time period; comparing the obtained MET data for the user to the guideline MET values in response to a determination that sufficient MET data is available, to determine whether the user has achieved the recommended level of physical activity; and outputting an adherence result indicating whether the user has achieved the recommended level of physical activity, in accordance with the result of the comparison.

The method can further comprise: deriving a value of an activity measure from the MET data; comparing the value of the activity measure to one or more thresholds associated with a risk of one or more health conditions to determine whether the user is at risk of any of the one or more health conditions; and outputting a health risk result identifying any of the one or more health conditions to which the user may be at risk, according to the result of the comparison. The activity measure can be any suitable metric relating to the user's activity as determined from the MET data. For example, the activity measure can be: a measure of sedentary or non-sedentary time; a measure of calorie burn such as the Physical Activity Level (PAL); a measure of the total number of minutes of physical activity above a MET threshold in bouts of certain duration; and a measure of physical activity energy expenditure.

The method can further comprise: obtaining user state information relating to a state of the user when the MET data was captured, wherein determining whether sufficient MET data is available can comprise: determining a length of an inactive time period in which the user state information indicates an inactive state during said one of the plurality of days; in response to the inactive time period being longer than a threshold time, determining that sufficient MET data is available if MET data is available for at least a predefined fraction of a remaining part of said day, wherein the remaining part excludes the inactive time period; and in response to the inactive time period being shorter than the threshold time, determining that sufficient MET data is available if at least a predefined amount of MET data is available during the remaining part of said day.

The MET data can include data captured over a plurality of days and the method can further comprise: determining whether MET data is available for at least a minimum number of days within a time period, wherein the comparison to the guideline MET values is only performed for MET data captured during the time period in response to a determination that MET data is available for at least the minimum number of days.

The method can further comprise: determining whether the user has exceeded a limit set by the guidelines; and outputting a message indicating a time at which the limit was exceeded, in response to a determination that the user has exceeded the limit.

Outputting the indicator can comprise displaying the adherence result in the form of a message indicating whether the user has achieved the recommended level of physical activity.

The MET data for the user can include MET data captured substantially continuously over at least an 8-hour period.

In some embodiments, the healthcare guidelines can be CR guidelines. Furthermore, in some embodiments the guideline MET values can be individualised guideline MET values specific to the user.

According to the present invention, there is also provided a computer-implemented method of monitoring adherence to healthcare guidelines defining a recommended level of physical activity, the method comprising: retrieving guideline MET values relating to the recommended level of physical activity, from computer-readable memory; retrieving MET data for a user from computer-readable memory captured over a plurality of days; using one or more processors, determining whether sufficient MET data is available by determining whether the obtained MET data includes at least a minimum amount of MET data within a defined time period; comparing the retrieved MET data for the user to the guideline MET values, in response to a determination that sufficient MET data is available, to determine whether the user has achieved the recommended level of physical activity; and using one or more processors, outputting an adherence result indicating whether the user has achieved the recommended level of physical activity, in accordance with the result of the comparison.

A computer-readable storage medium can be configured to store computer program instructions which, when executed by one or more processors, causes the one or more processors to perform any of the methods disclosed herein.

BRIEF DESCRIPTION OF THE DRAWINGS

Embodiments of the present invention will now be described, by way of example only, with reference to the accompanying drawings, in which.

DETAILED DESCRIPTION

Figure 1:
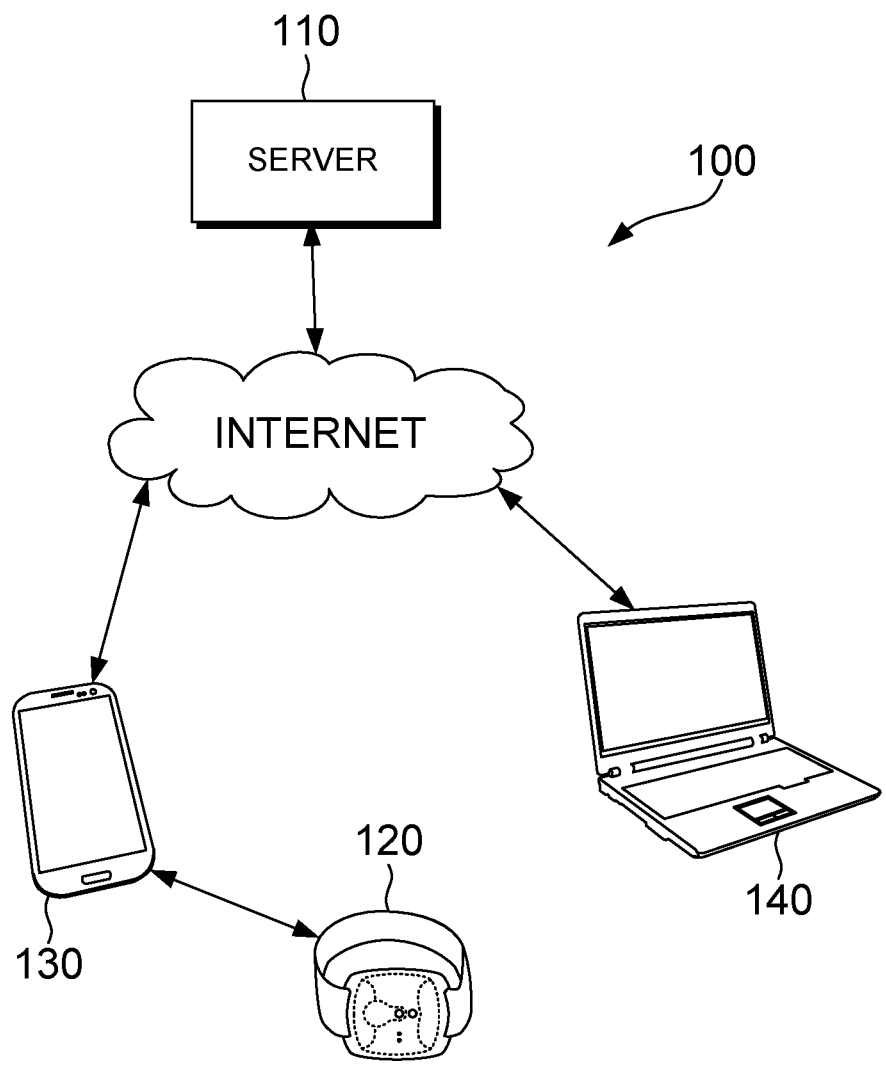
FIG. 1 illustrates a CR monitoring system for monitoring adherence to a CR regime, according to an embodiment of the present invention.

Referring now to FIG. 1, a CR monitoring system for monitoring adherence to a CR regime is illustrated, according to an embodiment of the present invention. The system of FIG. 1 can be used to monitor the user's behaviour in a free-living environment, that is to say, outside of supervised exercise sessions. The system is capable of analysing data captured substantially continuously over an extended period of time, for example 24 hours or longer. By substantially continuously, it is meant that the data is captured continuously for long periods of time with only occasional interruptions, for example when the user removes a wearable sensor to take a bath or a shower.

As shown in FIG. 1, the system 100 comprises a server 110, a wearable MET sensor 120, a smartphone 130, and a display device 140. Although a laptop computer 140 is illustrated in FIG. 1, in related embodiments the display device 140 could be any suitable Internet-enabled device which incorporates a display unit, for example a desktop or tablet computer, or a connected television. The wearable MET sensor 120 is arranged to be easily removed by the user.

In the present embodiment, the wearable MET sensor 120 is configured to communicate with the smartphone 130 over a wireless link such as a WiFi, Bluetooth or Zigbee link. The smartphone 130 is configured to communicate with the server 110 over a mobile telecommunications network, for example a third-generation (3G) or Long Term Evolution (LTE) network. The laptop computer 140 is configured to communicate with the server 110 via the Internet, through a WiFi network connection. However, embodiments of the invention are not limited to these particular types of communication link. In general, any of the communication links between devices shown in FIG. 1 can be implemented as a wired or wireless connection, using any suitable technology.

Continuing with reference to FIG. 1, the wearable MET sensor 120 is configured to be worn by a user during everyday activities, and to record MET data continuously at regular intervals. For example, the wearable MET sensor 120 can be provided in the form of an armband to be worn underneath the user's clothing. In the present embodiment the wearable MET sensor 120 records a MET data point every minute, although in other embodiments any suitable sampling rate can be used. Selecting a higher sampling rate will provide finer resolution in the captured data, but increase the volume of data to be transmitted, processed and stored.

Devices for obtaining MET data are known in the art, and to preserve brevity a detailed description will not be provided here. In the present embodiment, the wearable MET sensor is a multi-sensor device manufactured by BodyMedia, Inc.® comprising four sensors; tri-axial accelerometer, skin temperature, heat flux, and galvanic skin response sensors. The data collected from all four sensors is passed through BodyMedia's proprietary algorithms to calculate calorie burn, from which the MET is derived.

In the present embodiments, the wearable MET sensor 120 is configured to periodically attempt to upload data to a compatible local device, such as the smartphone 130 or laptop computer 140. The local device 130, 140 can then upload the received MET data for the user to the server 110. In other embodiments, a user can choose to connect the wearable MET sensor 120 to a local device in order to upload data at any time, for example by connecting the wearable MET sensor 120 to the laptop computer 140 via a Universal Serial Bus (USB) cable. New data points can be uploaded as and when they are recorded by the wearable MET sensor 120, or can be uploaded at pre-programmed time intervals, for example once every hour. In this way, the server 110 is able to collect MET data for the user.

Figure 10:
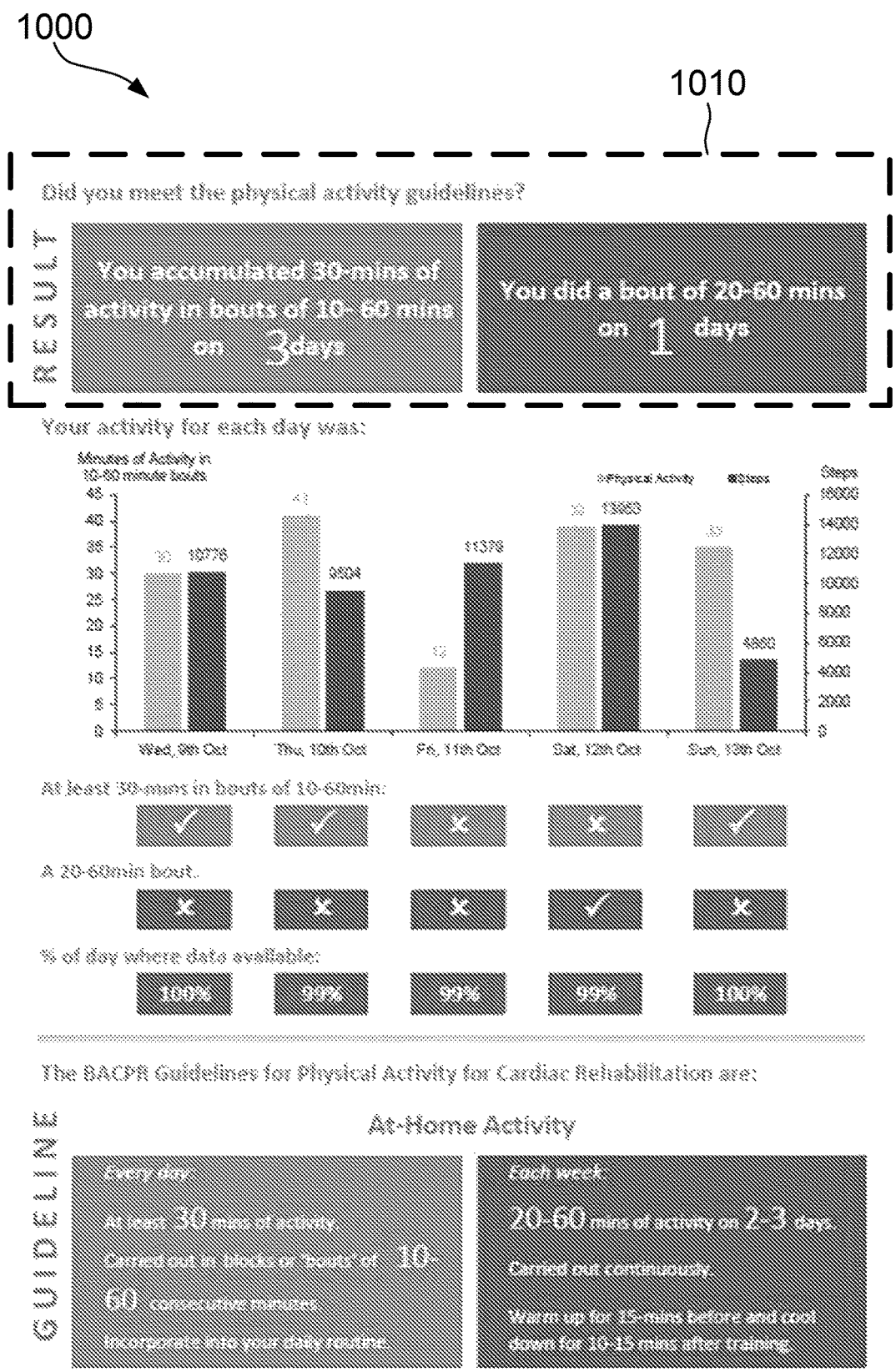
FIG. 10 illustrates a user interface for displaying an adherence result, according to an embodiment of the present invention.

The server 110 is configured to obtain guideline MET values defining a recommended level of physical activity for the CR regime, and to compare the received MET data to the guideline MET values to determine whether the user has achieved the recommended level of physical activity. The server 110 is also configured to output an adherence result to the display device 140 indicating whether the user has achieved the recommended level of physical activity, in accordance with the result of the comparison. In the present embodiment the adherence result takes the form of a message displayed on the screen of the display device 140, which indicates whether the user has achieved the recommended level of physical activity. FIG. 10 shows an example of a user interface screen 1000 which can be displayed by the display device 140, including the message 1010 indicating whether the recommended level of physical activity has been achieved. Depending on the embodiment, the device through which the adherence result is outputted may be the same device through which user MET data is uploaded, or may be a separate device.

The guideline MET values can define the recommended level of physical activity in terms of a number of sessions of specified duration and intensity. Each session may also be referred to as a 'bout' of physical activity. The intensity level for each session can be defined in terms of upper and lower MET values, which denote the recommended maximum and minimum intensity levels for that session. The duration for each session can also be expressed in terms of upper and lower limits. The guidelines can vary between different CR regimes, and in general, any number of sessions of any intensity can be defined. The exemplary user interface shown in FIG. 10 uses the British Association for Cardiovascular Prevention and Rehabilitation (BACPR) guidelines, which recommend at least 30 minutes of physical activity each day in blocks of between 10-60 consecutive minutes, with an additional bout of 20-60 minutes on 2 to 3 days each week. However, embodiments of the invention are not limited to monitoring adherence to the BACPR guidelines. It will be understood from reading the present disclosure that the general principles of the invention can be applied to any set of guidelines, for any CR programme or other type of healthcare regime.

As described earlier, the guidelines for conventional CR regimes normally define a recommended intensity level in terms of heart rate or a subjective measure, such as the Borg RPE or CR10 scales. In embodiments of the present invention where adherence to such guidelines is to be monitored, guideline MET values can be defined based on the existing guideline values, which could be expressed as heart rate, RPE or CR10 values.

An example of a method for obtaining guideline MET values from CR guidelines for a specific individual is as follows. As described above, CR guidelines can define intensity levels in terms of certain measures (e.g. heart rate; Borg RPE; CR10) equivalent to thresholds of an individual's $VO_2$ max, for example 40%, 60% and 70%. First, the individual's $VO_2$ max is estimated. Various methods of estimating an individual's $VO_2$ max are known, including an Incremental Shuttle Walk Test (ISWT) method from Fowler, Singh and Revill (2005) in which the $VO_2$ max is calculated using the equation:

$$VO_2 \max(\text{ml kg}^{-1} \text{min}^{-1}) = 7.81 + [0.03 \times D]$$

where D is the total distance walked during the ISWT.

One MET is equivalent to 3.5 ml kg$^{-1}$ min$^{-1}$. Therefore the equivalent guideline MET values to 40%, 60% and 70% $VO_2$ max can then be calculated by dividing the corresponding $VO_2$ values by 3.5, as follows:

$$\text{MET equivalent of } 40\% VO_2 \max = [0.4 \times VO_2 \max]/3.5$$

$$\text{MET equivalent of } 60\% VO_2 \max = [0.6 \times VO_2 \max]/3.5$$

$$\text{MET equivalent of } 70\% VO_2 \max = [0.7 \times VO_2 \max]/3.5$$

A method such as the one described above can be used to obtain individualised guideline MET values specific to an individual user, when the healthcare guidelines define the recommended level of physical activity in terms of $VO_2$ max. A similar approach can also be used to obtain equivalent MET values when the healthcare guidelines are expressed in terms of different parameters, such as heart rate or RPE. The approach can also be extended to healthcare guidelines which define a recommended level of intensity using relative terms, for example, the guidelines from New Zealand define intensity using the terms "low", "moderate" and "vigorous". Equivalent MET values for the thresholds "low", "moderate" and "vigorous" can be defined for the general population. For example, 1 MET represents the number of calories burned per minute at rest. Activities of 1.8 MET can be defined as being equivalent to a "low" or "light" activity level. Similarly, 3 METs can be defined as being equivalent to a "moderate" level of activity, and 6 METs can be defined as being equivalent to a "vigorous" level of activity. It should be understood that these numbers are merely exemplary, and other MET values can be chosen in other embodiments. Once the guideline MET values have been obtained, they can be stored for future reference. For example, the server no in FIG. 1 can retrieve predetermined guideline MET values from a local storage unit or can query a remote database of guideline MET values. Although a method has been described above for calculating guideline MET values for a specific individual, based on the individual's $VO_2$ max, in other embodiments average guideline MET values could be used instead of being tailored to a specific individual. For example, the server could access a database containing typical guideline MET values for different types of individual, categorised according to such factors as age, gender, fitness level, and so on. For any given user, the most appropriate guideline values could be retrieved and used.

Figure 2:
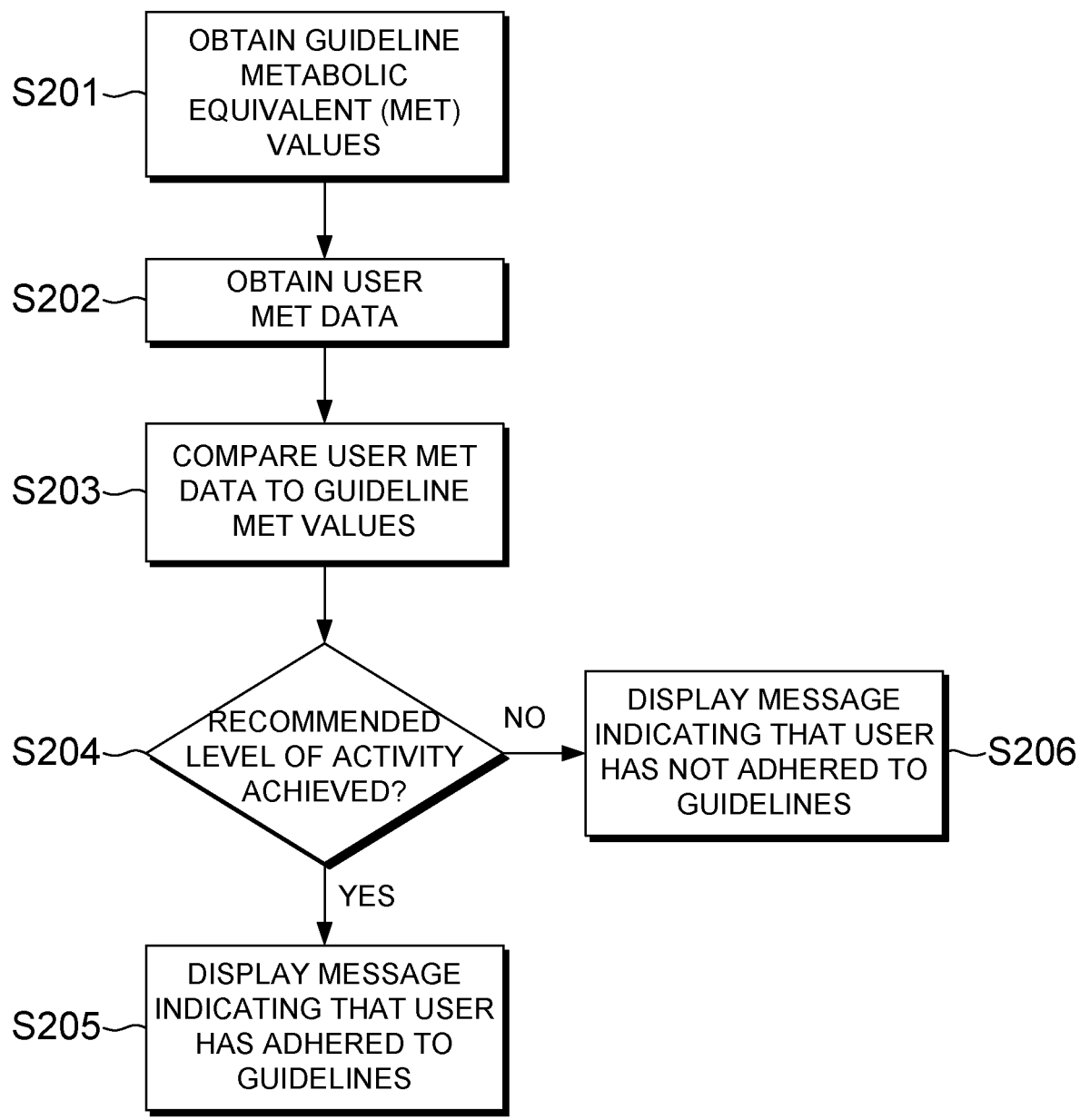
FIG. 2 is a flowchart showing a method of monitoring adherence to a CR regime, according to an embodiment of the present invention.
Figure 5:
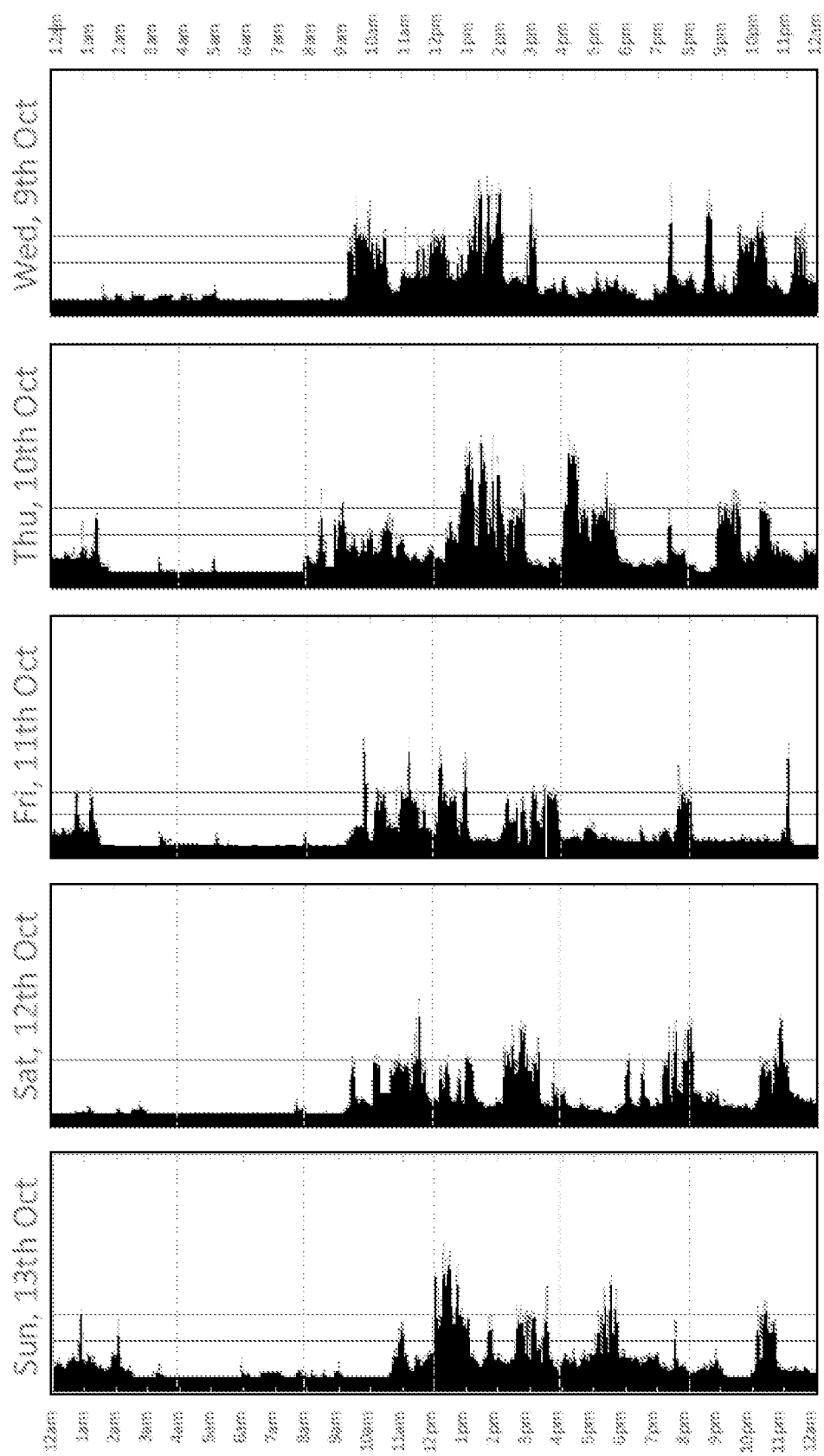
FIG. 5 illustrates MET data recorded over a plurality of days, according to an embodiment of the present invention.

Referring now to FIGS. 2 and 5, a method of monitoring adherence to a cardiac rehabilitation regime will now be described, according to an embodiment of the present invention. FIG. 2 is a flowchart illustrating the method, and FIG. 5 illustrates an example of MET data recorded over a plurality of days, which can be analysed using the method. The method can be implemented by the server 110 of FIG. 1, or by any suitable device in other embodiments. The method shown in FIG. 2 can be used to analyse user MET data captured in a free-living environment.

First, in step S201, the predefined guideline MET values defining a recommended level of physical activity for the CR regime are obtained. For example, in step S201 the guideline MET values could be input by a user, or could be retrieved from a storage unit housing computer-readable memory. Then, in step S202, MET data is obtained for a user. When the method is implemented in a server as shown in FIG. 1, step S202 can comprise receiving the MET data from a remote MET sensor over a suitable communications link, or can comprise retrieving previously-uploaded data from a storage unit.

Next, in step S203 the user MET data is compared to the guideline MET values to determine whether the user has achieved the recommended level of physical activity. When the recommended level of physical activity is defined in terms of one or more bouts of physical activity at an intensity level between specified upper and lower MET limits, the user MET data can be scanned for any periods of continuous physical activity within the upper and lower MET limits. When a period of physical activity is found in the MET data with an intensity between the upper and lower MET limits, the duration of the observed period of physical activity is compared to a recommended duration set by the guidelines, which may be expressed as an absolute value, for example 30 minutes, or in terms of upper and lower time limits, for example 10 to 60 minutes. The total number of periods matching the duration and intensity limits defined by the guidelines can be counted, to determine whether the user has achieved the recommended level of physical activity, that is, the recommended number of bouts of physical activity.

After comparing the user MET data to the guideline MET values, an adherence result is outputted to indicate whether the user has achieved the recommended level of physical activity, in accordance with the result of the comparison. In the present embodiment, the adherence result is displayed in the form of a message indicating whether the user has achieved the recommended level of physical activity. However, other approaches are possible. For example, in other embodiments the adherence result could be outputted as a simple audio or visual alert to the user, as an email to a pre-selected email address, or as a text message to a pre-selected telephone number. For example, the email address or telephone number of the user and/or their physician could be provided.

In step S204, if the recommended level of physical activity has been achieved, then in step S205 a message indicating that the user has achieved the level of physical activity is displayed. On the other hand, if in step S204 the recommended level of physical activity has not been achieved, then in step S206 a message indicating that the user has not achieved the level of physical activity is displayed.

MET values are an objective measure of the intensity of the physical activity being performed by the individual, as the MET values are derived directly from calorie burn data. The use of MET values to monitor adherence to healthcare guidelines therefore represents a significant improvement over the prior art methods, which use less reliable, subjective, measures such as heart rate and RPE.

Additionally, as described above, a method such as the one shown in FIG. 2 can be used to analyse data recorded substantially continuously over an extended period of time, in a free-living environment. Preferably, MET data is recorded over a substantial part of the waking day, for example at least 8 hours, to provide an accurate indicator of the user's daily routine. By using data collected in a free-living environment, an adherence result is obtained that takes into account the user's physical activity outside of any structured exercise sessions. This represents a significant improvement over prior art approaches which rely on structured exercise sessions, and can often give a false negative result because the system fails to take into consideration physical activity outside of the prescribed exercise sessions. In contrast, embodiments of the present invention provide more reliable systems and methods for determining whether or not a patient is meeting the required level of physical activity.

A method such as the one shown in FIG. 2 can be implemented using a computer, by retrieving guideline MET values defining a recommended level of physical activity for the CR regime, from computer-readable memory, retrieving MET data for a user from computer-readable memory, using one or more processors to compare the retrieved MET data for the user to the guideline MET values to determine whether the user has achieved the recommended level of physical activity, and using one or more processors to output an adherence result indicating whether the user has achieved the recommended level of physical activity, in accordance with the result of the comparison.

Figure 3:
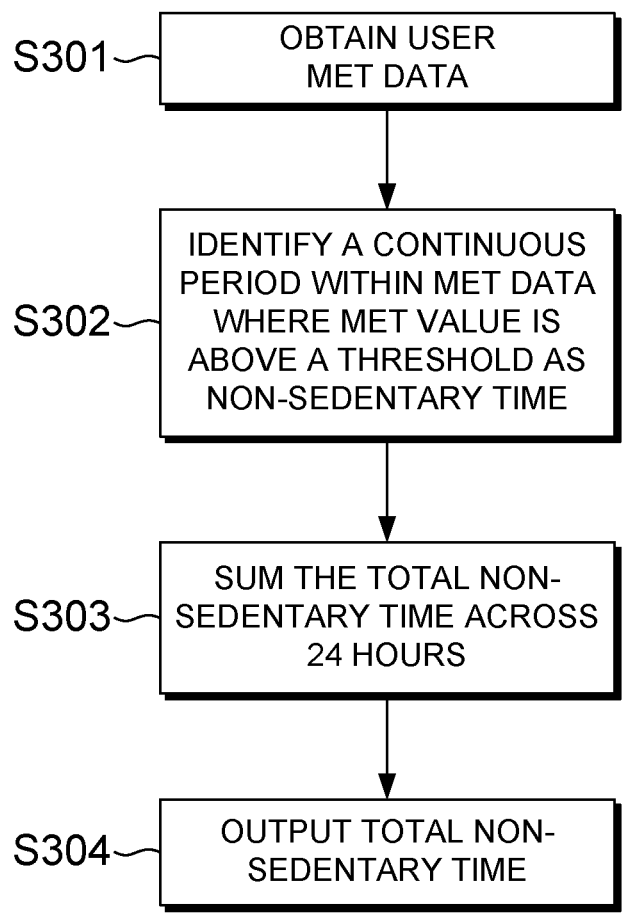
FIG. 3 is a flowchart showing a method of determining non-sedentary time from MET data, according to an embodiment of the present invention.

Referring now to FIG. 3, a flowchart showing a method of deriving a value of an activity measure from the MET data is illustrated, according to an embodiment of the present invention. In the present embodiment the activity measure is the total amount of non-sedentary time within a 24-hour time period, however, in other embodiments a different activity measure may be derived. Non-sedentary time is defined as any period of time in which the user is performing physical activity above a certain threshold level. Similarly, sedentary time can be defined as any period of time in which the user's level of activity is below the threshold.

First, user MET data is obtained in step 301. The MET data is obtained in the same way as explained above with reference to step S202 of FIG. 2. In step S302, non-sedentary time in the MET data is identified by searching for any continuous periods within the MET data where the MET value is above a threshold. In some embodiments, a minimum duration may be required for a period to be counted as a 'continuous' period of non-sedentary time. Each continuous period of non-sedentary time may also be referred to as a 'bout' of activity. In step S302, more than one non-sedentary time period may be identified if multiple such periods are detected.

Then, in step S303 the total amount of non-sedentary time across the identified bouts of activity may be determined by summing the duration of any non-sedentary time periods identified in step S302 across a 24 hour period. In other words, at step S303, a single value is obtained which represents the total amount of non-sedentary time within one day. In some embodiments step S303 may be omitted, for example when only a single non-sedentary period is identified. Alternatively, when a plurality of periods are identified, the duration of each individual sedentary time period may be counted and outputted separately.

Then, in step S304 the total non-sedentary time is outputted, for example by displaying a message indicating the total amount of non-sedentary time, or by outputting the value of the total non-sedentary time to another device or to a software module.

Figure 4:
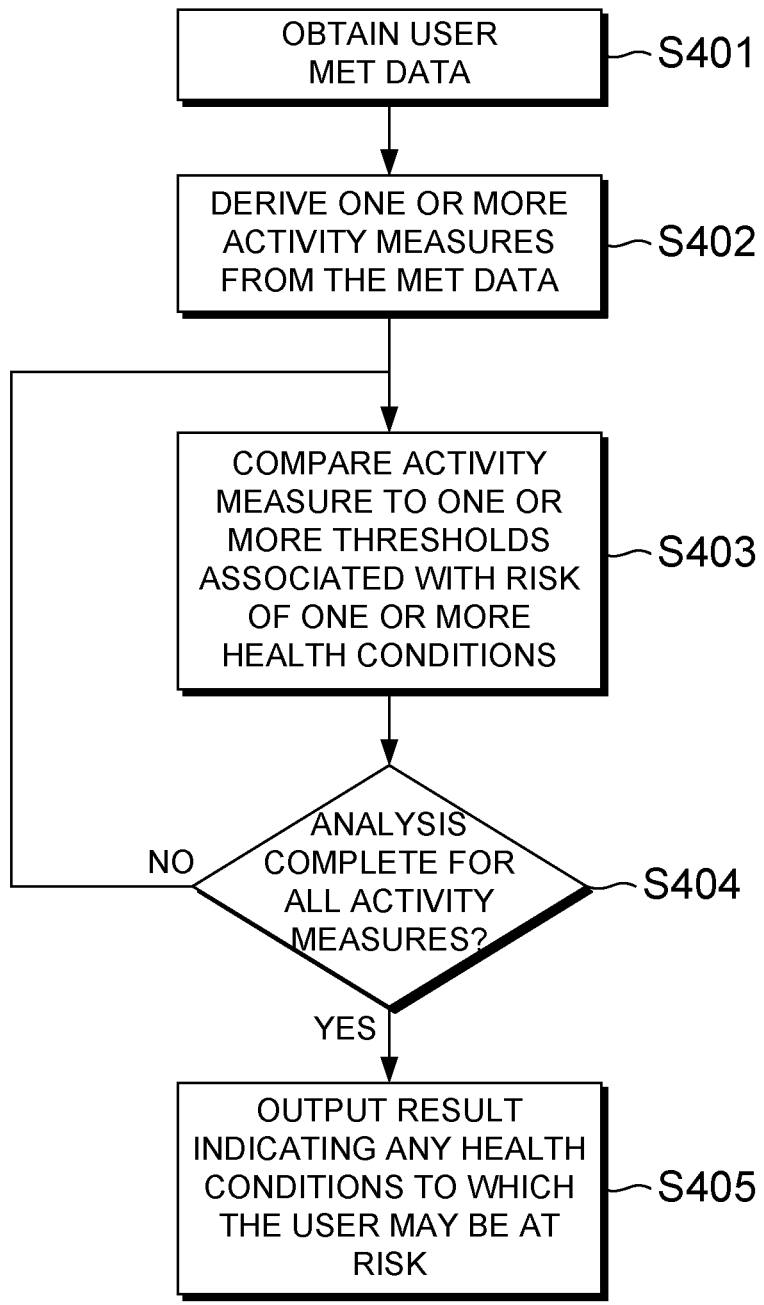
FIG. 4 is a flowchart showing a method of determining which diseases to which a user is at risk, according to an embodiment of the present invention.

Referring now to FIG. 4, a flowchart showing a method of determining one or more health conditions to which a user may be at risk is illustrated. The health conditions may include, for example, type-2 diabetes, cardiovascular disease, colon cancer, and obesity. Each of these health conditions may be associated with different risk factors. For example, one risk factor for type-2 diabetes is the total amount of non-sedentary time per day. A total non-sedentary time of ≥40% of the number of waking hours during the day is associated with an increased risk of type-2 diabetes.

First, user MET data is obtained in step S401. The user MET data can be obtained in the manner referred to above with reference to step S202 in FIG. 2.

Then, in step S402 a value is derived for each of one or more activity measures from the MET data. The activity measure may be a total length of non-sedentary time, as described above with reference to FIG. 3. Other examples of activity measures that can be derived in embodiments of the present invention include: a measure of calorie burn such as the PAL; a measure of the total number of minutes of physical activity above a MET threshold in bouts of certain duration; and a measure of physical activity energy expenditure. However, embodiments of the invention are not limited to these particular activity measures, and in other embodiments any suitable metric relating to the user's activity as determined from the MET data may be used as an activity measure.

In step S403, the value of one of the activity measures is compared to one or more thresholds associated with a risk of one or more health conditions to determine whether the user is at risk of any of the one or more health conditions. For example, in step S403 an external server storing a list of health conditions and associated thresholds may be queried. Alternatively, step S403 may use a lookup table stored in local memory to retrieve the thresholds for a particular activity measure. The thresholds can be defined based on known risk factors associated with one or more diseases.

Examples of thresholds for a PAL activity measure, with associated health conditions, are shown below in Table 1. In the present embodiment, the thresholds are defined based on data from the Food and Agriculture Organisation of the United Nations, World Health Organisation, and United Nations University (FAO/WHO/UNU; 2004), in a document titled 'Human Energy Requirements, Report of a joint FAO/WHO/UNU Expert Consultation', Rome, 17-24 Oct. 2001. The PAL provides a measure of calorie burn, and can be calculated as the ratio of the average calorie burn per day, as determined from the MET data, to the resting metabolic rate (RMR) determined based on the user's profile (e.g. age/gender/height/weight).

TABLE 1

| Physical Activity Level | ASSOCIATED HEALTH CONDITIONS |
|---|---|
| ≥1.75 | No risk comments |
| ≥1.7 to <1.75 | Increased risk of weight gain and obesity |
| <1.7 | Increased risk of type-2 diabetes |
| | Increased risk of cardiovascular disease |
| | Increased risk of breast & colon cancers (women) |
| | Increased risk of colon cancer (men) |
| | Increased risk of weight gain and obesity |

As described above, other examples of activity measures that can be used to diagnose a risk of certain health conditions in embodiments of the invention include, but are not limited to, a measure of the total number of minutes of physical activity above a MET threshold in bouts of certain duration; and a measure of physical activity energy expenditure. For example, an 'Activity Bouts' metric can be defined as a measure of the total number of minutes of physical activity above a MET threshold in bouts of certain duration. Physical activity can be defined as a MET level above a MET threshold, for example at least 3 METs, and a continuous period of 10 minutes is counted as a bout of physical activity. In some embodiments, the total number of minutes included in such bouts of activity can be summed across one week to determine the value of the 'Activity Bouts' measure. An activity measure relating to the total physical activity energy expenditure can be calculated by using the MET data to determine the total calories burnt during bouts of moderate physical activity, which can be identified as described above for an 'Activity Bouts' metric.

In step S404, it is checked whether the analysis has been completed for all activity measures for which values were derived in step S402. If any activity measures have not yet been analysed, then the process returns to step S403 and compares the next one of the activity measures to the corresponding thresholds. Once all activity measures have been analysed, the process proceeds to step S405.

If it has been determined in step S403 that the user may be at risk of one or more of the health conditions, then in step S405 a health risk result is outputted according to the result of the comparison in step S403. In the present embodiment, the health risk result is outputted by displaying a message to indicate any of the health conditions to which the user may be at risk. The message may also provide instructions to the user regarding steps that may be taken to reduce their risk of contracting the health conditions. In other embodiments, a different output mechanism may be used. For example, an audio message may be used for visually-impaired users, and/or the health risk result may be automatically recorded in a patient database for the current user.

In some embodiments, if it is determined that the user is not at risk of one of the health conditions, then in step S405, a message is displayed indicating that the user's current level of physical activity is not increasing their risk of the one or more health conditions.

Figure 6:
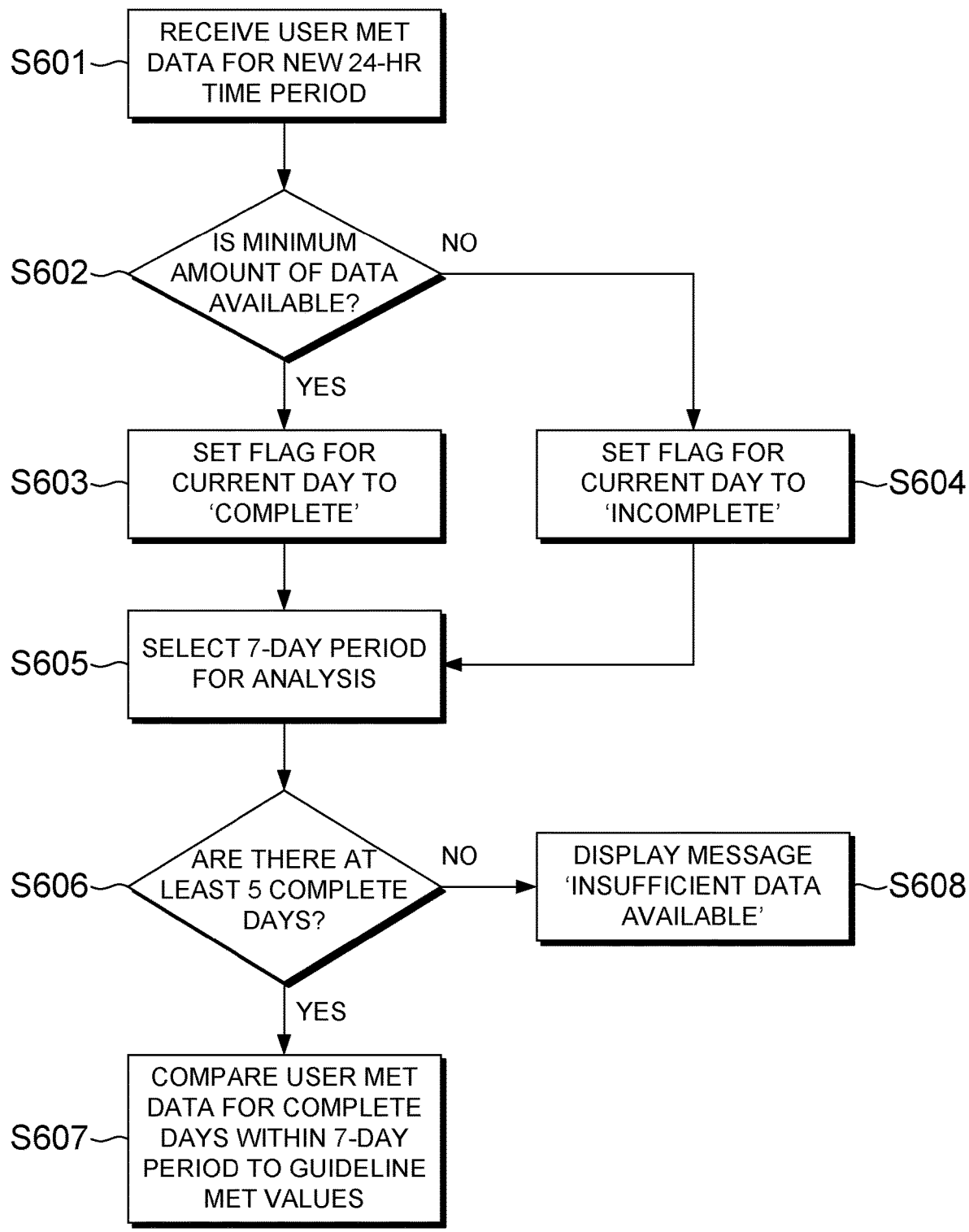
FIG. 6 is a flowchart showing a method of determining whether sufficient data is available to determine whether a user has adhered to the CR regime, according to an embodiment of the present invention.

Referring now to FIG. 6, a flowchart showing a method of determining whether sufficient data is available to determine whether a user has adhered to the CR regime is illustrated, according to an embodiment of the present invention. A method such as the one shown in FIG. 6 can be used when the guidelines for a CR regime require physical activity to be monitored over a certain time period, such as one week. The method will be described with reference to the BACPR guidelines, which define a recommended level of physical activity in terms of a specific number of bouts per week. However, in another embodiment of the invention, a similar method could be applied to guidelines in which the physical activity level is defined with respect to a different time period, for example one day or one month.

First, in step S601 user MET data is received for a new 24 hour period. As described above, the MET data may have been recorded continuously over the 24 hour period, or may have only been recorded intermittently. In step S602, it is checked whether sufficient MET data is available for the day in question. Here, depending on the embodiment, a fixed or variable minimum amount of data may be defined for determining whether sufficient MET data exists. The amount of data can be expressed in terms of the length of time for which data has been recorded. If the received MET data is incomplete, for example if the user has removed the wearable MET sensor during the day or if the sensor has malfunctioned, it is possible that the minimum amount of data may not have been received.

If sufficient data is available for the day currently being analysed, then in step S603 a flag is set to indicate that the current day is 'complete', that is, that a sufficiently complete set of data is available for that day. On the other hand, if insufficient data exists, then in step S604 the flag is set to indicate that the current day is 'incomplete'.

Next, in step S605, one week's worth of data is selected for analysis. One week is chosen in the present example because the BACPR guidelines specify the required level of physical activity in terms of a certain number of bouts per week. In other embodiments, a different time period could be chosen in step S605. In some embodiments, if the guidelines only define the physical activity level on a daily basis, then steps S605 and S606 could be omitted.

In step S606, it is checked whether there are at least five complete days within the seven-day period selected in step S605. That is, it is checked whether at least five days within that week are flagged as 'complete'. If MET data is available for at least five complete days within the selected time period, then in step S607 the process continues and compares the user MET data for any complete days within the selected time period to the guideline MET values, as described above. In response to a determination that there are not enough complete days available in step S607, then in S608 a message is displayed to inform the user that insufficient data is available. This message can prompt the user to take appropriate action, for example, to ensure that they wear the sensor for a longer period each day in order to record more MET data. Although a period of one week and a threshold of five days are used in the present embodiment, in other embodiments different time periods and thresholds can be chosen, as appropriate for the particular guidelines being monitored.

In this way, the comparison to the guideline MET values is only performed for the MET data captured on said one of the plurality of days in response to a determination in step S602 that sufficient MET data is available, since only the MET data from 'complete' days is analysed in step S607. Also, the comparison to the guideline MET values is only performed at all in response to a determination in step S606 that MET data is available for at least the minimum number of days.

By including these checks, the system can avoid analysing data and outputting a false negative result when insufficient data has been collected to be representative of the user's daily routine. This is an important consideration when analysing data collected in a free-living environment.

Figure 7:
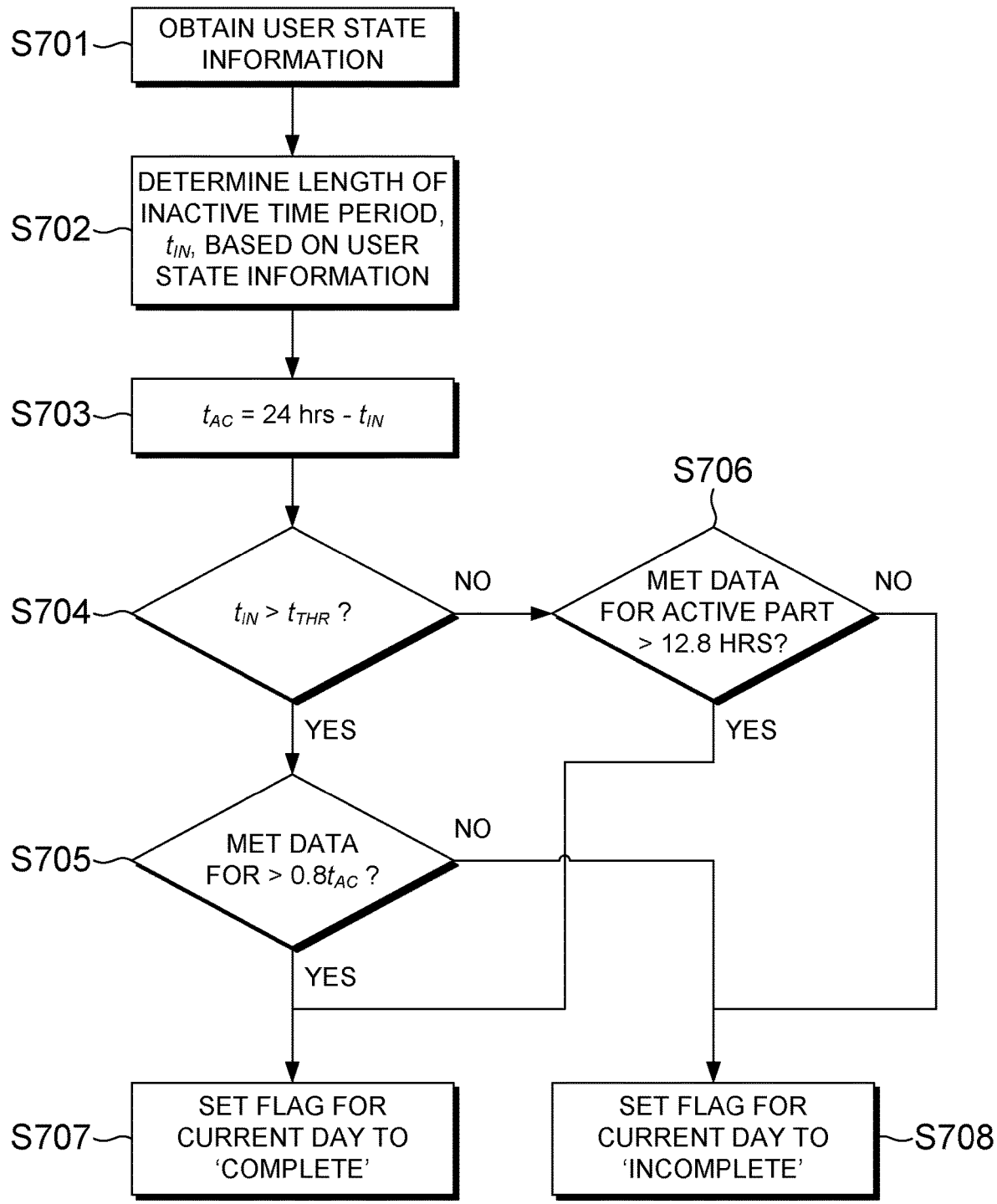
FIG. 7 is a flowchart showing a method of determining whether sufficient data is available for a 24-hour period, according to an embodiment of the present invention.

Referring now to FIG. 7, a flowchart showing a method of determining whether sufficient data is available for a 24-hour period is illustrated, according to an embodiment of the present invention. The method can be used to check whether sufficient data is available for any given day, and can be applied in step S602 of FIG. 6, for example.

First, in step S701 the system obtains user state information relating to a state of the user when the MET data was captured. The user state information can include one or more flags indicating whether or not the wearable MET sensor is being worn by the user at any given time, and/or indicating whether the user is currently active (standing, walking, running etc.) or inactive (sleeping, lying down, etc.). The information about the current user state could be inputted by the user, or could be detected based on sensor data. For example, a tri-axial accelerometer could be used to detect whether the user is currently lying down or standing/walking. Depending on the embodiment, the user state information may only distinguish between an inactive state and an active state, or may distinguish between different types of active and/or inactive state. Examples of different active states could include standing, walking, or running, whilst examples of different inactive states could include sleeping or lying down.

Next, in step S702 the length of an inactive time period is determined based on the user state information. The inactive time period is defined as a time period, during said one of the plurality of days, in which the user state information indicates an inactive state. The length of the inactive time period, $t_{IN}$, is taken as being representative of the length of time during that day in which the user was resting, whether asleep or lying down. In the present embodiment, the length of the inactive time period is calculated by counting the number of data points during the current day for which the user state information indicates an inactive state. The total inactive time during the day may include several periods of inactivity, and does not have to be a single continuous period. For example, the user state may be recorded as inactive while the user is sleeping during the night, and may also be recorded as inactive if the user rests at any point during the day.

Then, in step S703 the length of a remaining part of the day is determined, by subtracting the inactive time period $t_{IN}$ from 24 hours. The remaining part of the day excludes the inactive time period, represents the length of the waking day which is the period in which the user was awake and active. The remaining part of the day can also be referred to as the active period $t_{AC}$.

In step S704 it is checked whether the length of the inactive time period is longer than a threshold time $t_{THR}$. In response to the inactive time period being longer than the threshold time, in step S705 it is checked whether MET data is available for at least 80% of the remaining part of the day. Although 80% is used in the present embodiment, this is merely an example, and different fractions of the remaining part of the day could be defined in other embodiments.

If MET data is available for at least 80% of the remaining part, then sufficient MET data is available, and in step S707 the flag for the day being analysed is set to 'complete'. On the other hand, if MET data is only available for less than 80% of the remaining part, then there is insufficient data for the current day, and the flag is set to 'incomplete' in step S708.

In response to a determination in step S704 that the inactive time period is shorter than the threshold time, then in step S706 it is checked whether at least a predefined amount of MET data is available during the remaining part of the day. The predefined amount is a fixed threshold which does not depend on the length of the remaining part of the day. In the present embodiment, a fixed threshold of 768 minutes is used (12.8 hours), which corresponds to 80% of a typical 16-hour waking day. In other embodiments, a different value could be chosen for the fixed threshold.

If MET data is available for at least 768 minutes in the remaining part of the day, then it is determined that sufficient MET data is available, and in step S707 the flag for that day is set to 'complete'. If insufficient data is available, then in step S708 the flag is set to 'incomplete'.

The effect of the method of FIG. 7 is to increase the minimum amount of data required for a day to be flagged as 'complete' as the length of the user's waking day increases, up to a certain point. Once the length of the waking day exceeds a certain threshold, which in the present example is 16 hours, the system applies a fixed minimum amount as opposed to using a fraction of the waking day. This approach can be advantageous in ensuring that a day can still be classed as 'complete' even when the user state is incorrectly recorded as active while the user is asleep or lying down, causing the length of the waking day to be overestimated.

Figure 8:
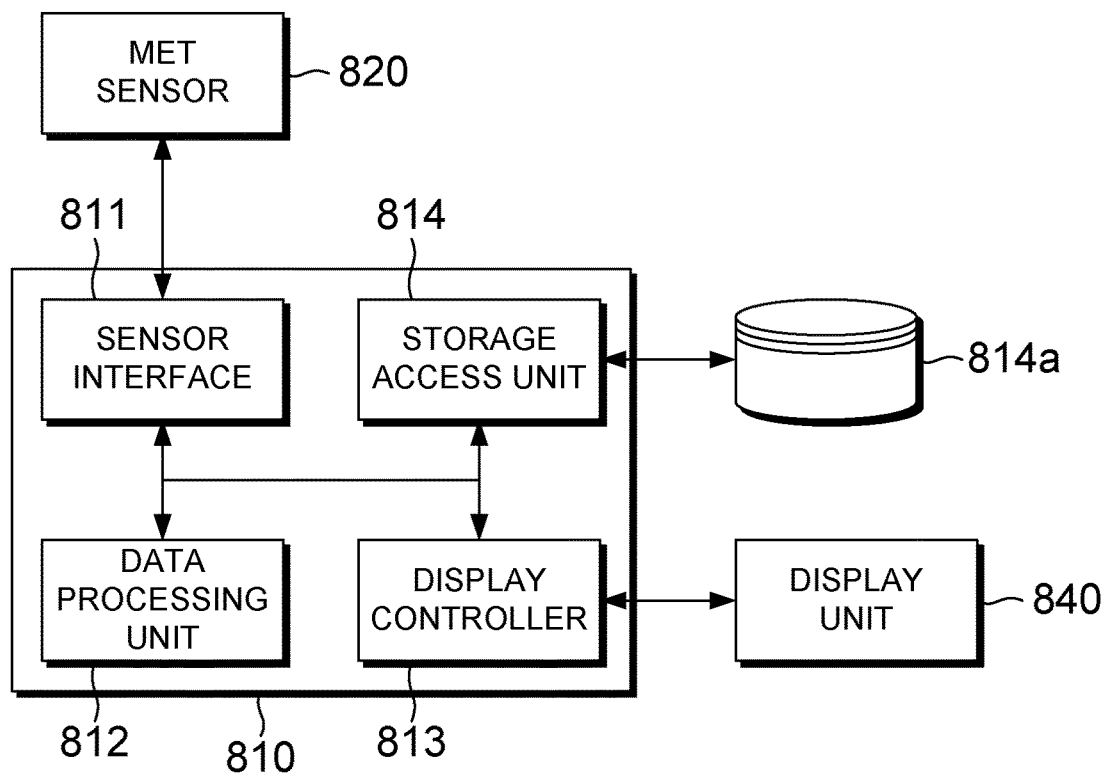
FIG. 8 illustrates a CR monitoring system embodied in a server, according to an embodiment of the present invention.
Figure 9:
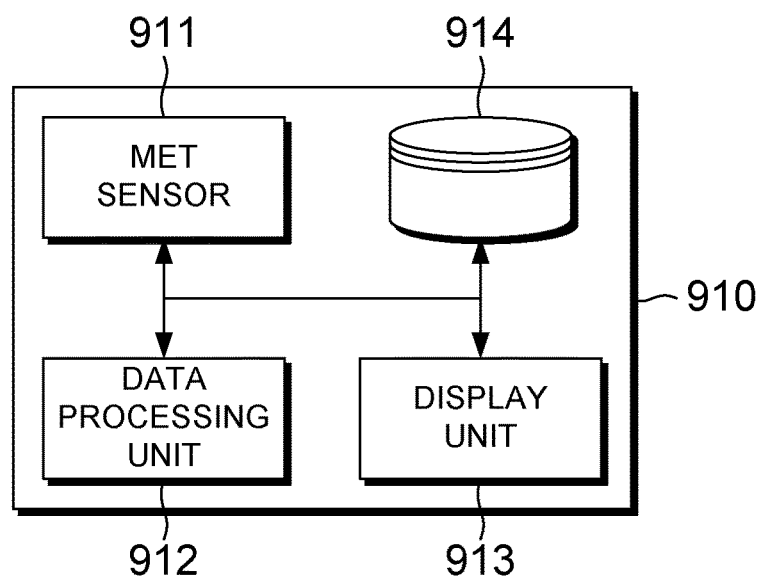
FIG. 9 illustrates a CR monitoring system embodied as a stand-alone device, according to an embodiment of the present invention.

Referring now to FIGS. 8 and 9, systems for monitoring adherence to CR regime are illustrated according to embodiments of the present invention. The systems of FIGS. 8 and 9, along with the system of FIG. 1, may also be referred to as CR monitoring systems. The system of FIG. 8 is embodied as a server connected to a plurality of external devices, whilst the system of FIG. 9 is embodied as a stand-alone device.

In the embodiment of FIG. 8, a server 810 comprises a sensor interface 811, a data processing unit 812, display controller 813, and a storage access unit 814. The sensor interface is configured to obtain MET data for a user from a MET sensor 820, which could be a wearable MET sensor such as the one shown in FIG. 1. The sensor interface 811 could receive the MET data directly from the MET sensor 820, or could receive the data via an intermediate device local to the MET sensor 820, such as the laptop or smartphone shown in FIG. 1. Depending on the embodiment, the connection between the sensor interface 811 and the MET sensor 820 may be wired or wireless. The storage access unit 814 is configured to access data, for example stored MET data and/or guideline MET values, from a storage unit 814a. The display controller 813 is configured to control a separate display unit 840, which could be included in a suitable display device such as the laptop computer shown in FIG. 1.

The embodiment of FIG. 9 differs from FIG. 8 in that the MET sensor 911, display unit 913, and storage unit 914 are included in the same physical device as the data processing unit 912. The device 910 could be embodied as a smartphone, for example, or as a wearable monitoring device such as the one shown in FIG. 1, with the addition of a display unit.

The data processing unit 812, 912 is configured to receive the guideline MET values from the storage access unit 814, 914, and to compare the received MET data to the guideline MET values to determine whether the user has achieved the recommended level of physical activity. The data processing units 812, 912 of FIGS. 8 and 9 can be configured to perform any of the above-described methods for analysing user MET data. The display controller 813 of FIG. 8 and the display 913 of FIG. 9 are configured to output an adherence result indicating whether the user has achieved the recommended level of physical activity, in accordance with the result of the comparison. For example, the display controller 813 can display the adherence result using the user interface shown in FIG. 10.

The sensor interface 811 of FIG. 8 and the MET sensor 911 of FIG. 9 can both be referred to as data collection units. In the embodiment of FIG. 8, the data collection unit is embodied as a wireless network interface configured to receive the MET data over a network connection. In the embodiment of FIG. 9, the data collection unit comprises a MET sensor arranged to directly capture the MET data.

Figure 11:
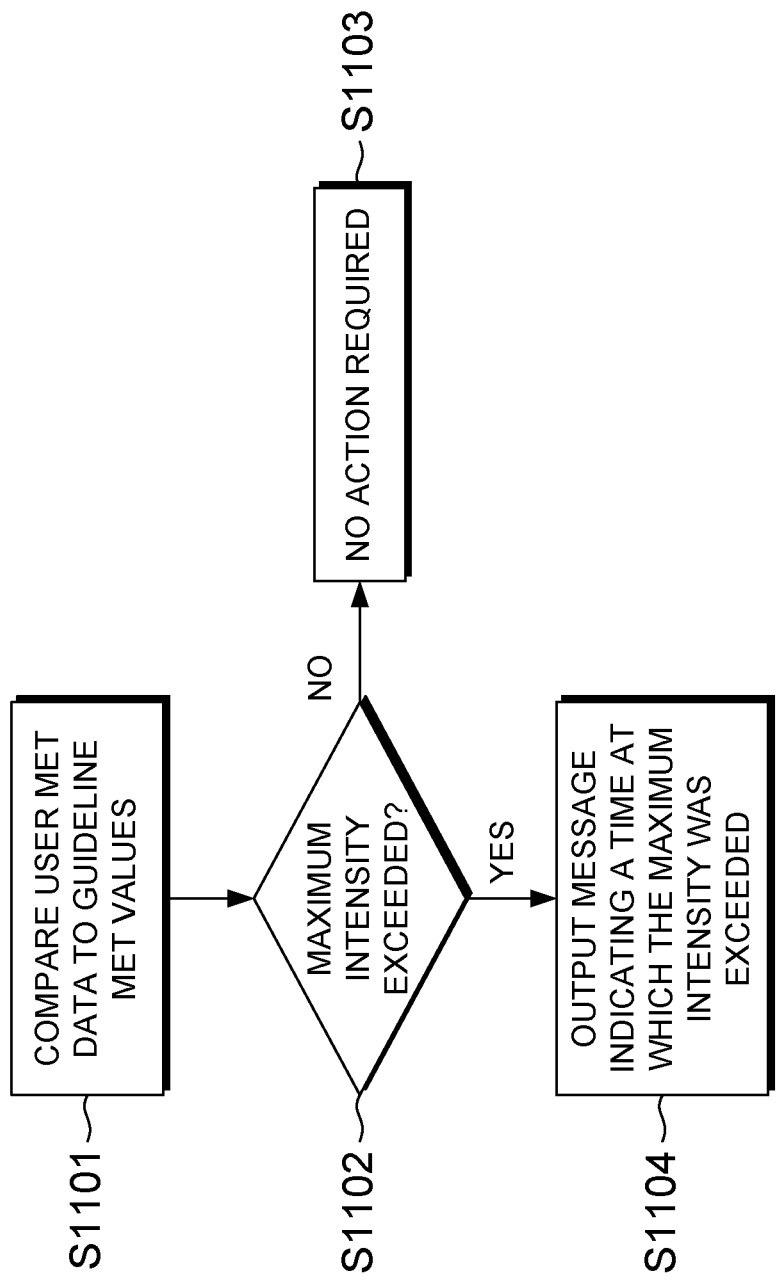
FIG. 11 is a flowchart showing a method of alerting a user when a recommended maximum intensity level is exceeded, according to an embodiment of the present invention.

Referring now to FIG. 11, a flowchart is illustrated showing a method of alerting a user when a recommended maximum intensity level is exceeded, according to an embodiment of the present invention. The method can be implemented in any of the above-described embodiments. First, in step S1101, user MET data is compared to guideline MET values, using any of the above-described methods.

During the comparison, in step S1102 it is checked whether the user has exceeded a recommended maximum intensity level defined by the MET guideline values. If the user has not exceeded the maximum intensity level, then no action is required and the process terminates in step S1103. However, in response to a determination that the user has exceeded the recommended maximum intensity level, then in step S1104 a message indicating a time at which the recommended maximum intensity level was exceeded is outputted. This enables a user to identify the activity that they were performing at the time when the maximum intensity level was exceeded, so that they can avoid that activity in future.

Although a maximum intensity level is used in the embodiment of FIG. 11, in other embodiments any limit set by the healthcare guidelines could be used. For example, an upper or lower limit of the duration for a bout of physical activity could be monitored, and the user alerted if a bout is detected which exceeds either the minimum (i.e. lower than the minimum) or the maximum (i.e. higher than the maximum) recommend duration. Similarly, a minimum intensity level could be monitored as a lower limit, instead of or as well as monitoring a maximum intensity level as an upper limit. In response to any upper or lower limit being exceeded, the system can display information about the time at which the limit was exceeded. This can drive positive behavioural change, by enabling the user to identify the behaviour that caused the guideline limits to be exceeded.

Various methods have been described herein with reference to the accompanying figures. Depending on the embodiment, any of these methods may be implemented in dedicated hardware, such as an Application Specific Integrated Circuit (ASIC) or Field Programmable Gate Array (FPGA), or in software instructions in one or more computer programs. In some embodiments, a mixture of hardware and software may be used. In software implementations of the invention, a non-transitory computer-readable storage medium can be configured to store computer program instructions which, when executed by one or more processors, causes the one or more processors to perform any of the methods disclosed herein.

Embodiments of the invention have been described herein with reference to monitoring adherence to a CR regime. However, the present invention is not limited to use with CR regimes. In other embodiments, any of the systems and methods disclosed herein can be adapted to monitor adherence to any healthcare guidelines that define a recommended level of physical activity.

Whilst certain embodiments of the invention have been described herein with reference to the drawings, it will be understood that many variations and modifications will be possible without departing from the scope of the invention as defined in the accompanying claims.

The invention claimed is:

1. A system for monitoring adherence to healthcare guidelines defining a recommended level of physical activity, the system comprising at least one non-transitory computer-readable storage medium storing instructions that, when executed by at least one processor, cause the at least one processor to:
obtain metabolic equivalent (MET) data for a user over a time period comprising a plurality of days, wherein the obtained MET data comprises data captured by a wearable sensor configured to output the MET data continuously at regular intervals;
determine a length of a time period during which a user is awake on at least one day within the time period over which the MET data is obtained;
define a minimum length of time as a predefined fraction of the determined time period during which the user is awake;
determine whether sufficient MET data is available by determining whether the time period includes at least a minimum number of days on which the MET data is available for at least the defined minimum length of time per day during the time period during which the user is awake;
obtain guideline MET values relating to the recommended level of physical activity;
compare the MET data to the guideline MET values in response to a determination that sufficient MET data is available to determine whether the user has achieved the recommended level of physical activity; and
output an adherence result indicating whether the user has achieved the recommended level of physical activity, in accordance with the result of the comparison.

2. The system of claim 1, further comprising instructions that, when executed by the at least one processor, cause the processor to:
derive a value of an activity measure from the MET data;
compare the value of the activity measure to one or more thresholds associated with a risk of one or more health conditions to determine whether the user is at risk of any of the one or more health conditions; and
output a health risk result identifying any of the one or more health conditions to which the user may be at risk, according to the result of the comparison of the value of the activity measure to the one or more thresholds.

3. The system of claim 2, wherein the activity measure is one of:
a measure of sedentary or non-sedentary time;
a measure of calorie burn;
a measure of the total number of minutes of physical activity above a MET threshold in bouts of certain duration; and
a measure of physical activity energy expenditure.

4. The system of claim 1, further comprising instructions that, when comparing the received MET data to the guideline MET values, cause the at least one processor to determine whether the user has exceeded a limit set by the healthcare guidelines, and
wherein in response to a determination that the user has exceeded the limit, cause the processor to output a message indicating a time at which the limit was exceeded.

5. The system of claim 1, further comprising instructions that cause the at least one processor to control a display unit to display the adherence result in the form of a message indicating whether the user has achieved the recommended level of physical activity.

6. The system of claim 1, further comprising instructions that cause the at least one processor to obtain MET data captured substantially continuously over at least an 8-hour period.

7. The system of claim 1, further comprising a network interface configured to receive the MET data over a network connection.

8. The system of claim 1, further comprising a MET sensor arranged to directly capture the MET data, and/or wherein the healthcare guidelines are Cardiovascular Rehabilitation (CR) guidelines, and/or wherein the guideline MET values are individualised guideline MET values specific to the user.

9. A method of monitoring adherence to healthcare guidelines defining a recommended level of physical activity, the method comprising:
obtaining, by at least one processor, guideline MET values relating to the recommended level of physical activity;
obtaining, by the at least one processor, MET data for a user captured over a time period comprising a plurality of days, wherein the obtained MET data comprises data captured by a wearable sensor configured to output the MET data continuously at regular intervals;
determining a length of a time period during which a user is awake on at least one day within the time period over which the MET data is obtained;
defining a minimum length of time as a predefined fraction of the determined time period during which the user is awake;
determining, by the at least one processor, whether sufficient MET data is available by determining whether the time period includes at least a minimum number of days on which the MET data is available for at least the defined minimum length of time per day during the time period during which the user is awake;
comparing, by the at least one processor, the obtained MET data for the user to the guideline MET values, in response to a determination that sufficient MET data is available, to determine whether the user has achieved the recommended level of physical activity; and
outputting, by the at least one processor, an adherence result indicating whether the user has achieved the recommended level of physical activity, in accordance with the result of the comparison.

10. The method of claim 9, further comprising:
deriving, by the at least one processor, a value of an activity measure from the MET data;
comparing the value of the activity measure to one or more thresholds associated with a risk of one or more health conditions to determine whether the user is at risk of any of the one or more health conditions; and
outputting, by the at least one processor a health risk result identifying any of the one or more health conditions to which the user may be at risk, according to the result of the comparison of the value of the activity measure to the one or more thresholds.

11. The method of claim 10, wherein the activity measure is one of:
a measure of sedentary or non-sedentary time;
a measure of calorie burn;
a measure of the total number of minutes of physical activity above a MET threshold in bouts of certain duration; and
a measure of physical activity energy expenditure.

12. The method of claim 9, further comprising:
determining, by the at least one processor, whether the user has exceeded a limit set by the healthcare guidelines; and
outputting, by the at least one processor, a message indicating a time at which the limit was exceeded, in response to a determination that the user has exceeded the limit.

13. The method of claim 9, wherein outputting the indicator comprises displaying, by the at least one processor, the adherence result in the form of a message indicating whether the user has achieved the recommended level of physical activity.

14. The method of claim 9, wherein the MET data for the user includes MET data captured substantially continuously over at least an 8-hour period, and/or wherein the healthcare guidelines are CR guidelines, and/or wherein the guideline MET values are individualised guideline MET values specific to the user.

15. A computer-implemented method of monitoring adherence to healthcare guidelines defining a recommended level of physical activity, the method comprising:
retrieving, by at least one processor, guideline MET values relating to the recommended level of physical activity, from computer-readable memory;
retrieving, by the at least one processor, MET data for a user from computer-readable memory, wherein the MET data is captured over a time period comprising a plurality of days, wherein the obtained MET data comprises data captured by a wearable sensor configured to output the MET data continuously at regular intervals;
determining, by the at least one processor, a length of a time period during which a user is awake on at least one day within the time period over which the MET data is obtained;
defining, by the at least one processor, a minimum length of time as a predefined fraction of the determined time period during which the user is awake;
determining, by the at least one processor, whether sufficient MET data is available by determining whether the time period includes at least a minimum number of days on which the MET data is available for at least the defined minimum length of time per day during the time period during which the user is awake;
comparing, by the at least one processor, the retrieved MET data for the user to the guideline MET values, in response to a determination that sufficient MET data is available, to determine whether the user has achieved the recommended level of physical activity; and
outputting, by the at least one processor, an adherence result indicating whether the user has achieved the recommended level of physical activity, in accordance with the result of the comparison.

* * * * *